United States Patent [19]

Ritter

[11] 4,293,562

[45] Oct. 6, 1981

[54] METHODS OF OBTAINING ANOREXIC EFFECTS USING A COMBINATION OF AMPHETAMINES AND CIMETIDINE

[76] Inventor: Arnold Ritter, 18402 N. 19th Ave., Phoenix, Ariz. 85023

[21] Appl. No.: 53,766

[22] Filed: Jul. 2, 1979

[51] Int. Cl.³ ................. A61K 31/415; A61K 31/135
[52] U.S. Cl. ................................. 424/273 R; 424/330
[58] Field of Search ........................... 424/273 R, 330

[56] References Cited

U.S. PATENT DOCUMENTS

| | | | |
|---|---|---|---|
| 4,000,296 | 12/1976 | Durant et al. | 424/273 |
| 4,000,302 | 12/1976 | Blank et al. | 424/273 |
| 4,112,234 | 9/1978 | Chenshaw et al. | 424/273 |

OTHER PUBLICATIONS

The Merck Index, 9th ed. (1976) item A3 Merck & Co. Inc.
The Pharmacological Basis of Therapeutics-1966-pp. 500-503.
Chem. Abst. 85 29011v (1976)-Pounder et al.

*Primary Examiner*—Douglas W. Robinson
*Attorney, Agent, or Firm*—Harry M. Weiss

[57] ABSTRACT

A synergistic combination of ingredients and a method of using same to obtain weight reduction in mammalian hosts by appetite suppression while eliminating the adverse side effects heretofore associated with the administration and use of anorexants such as amphetamines and the like for anorexic therapy. A pharmaceutical preparation containing as its principal active ingredients, an anorexant mixed with cimetidine.

5 Claims, No Drawings thereby substantially eliminating the side effects caused thereby without diminishing the beneficial results thereof.

These and still further objects as shall hereinafter appear are fulfilled by the present invention in a remarkably unexpected fashion as will be readily discerned from the following detailed description and examples embodying the present invention.

The present invention is predicated upon my discovery that I can substantially reduce the amount of anorexant required to achieve anorexia by combining an anorexant in an amount substantially less than that normally required to obtain anorexia with cimetidine, to obtain a synergistic combination for the treatment of obesity in mammalian hosts.

In a preferred practice of the present invention, 300 mg of cimetidine (available from Smith, Kline and French under the brand name "TAGAMET") is mixed with 5 mg of dextroamphetamine sulfate (available from Smith, Kline and French under the brand name "DEXEDRINE"). The combination may be placed into a soft gelatin capsule or tableted with a conventional binder to provide a single daily dosage with which to practice the present invention. If desired, the effect of the present invention can be also obtained by simultaneously administering separate doses of the designated drugs in accordance with the regimens herein described.

As alternatives to dextroamphetamine sulfate in the practice of the present invention, satisfactory results are obtained by the use of other anorexants such as phenteramine resin (available under the brand name IONOMINE from Pennwalt); phenmetrazine (available under the brand name PRELUDIN from Boehringer-Ingelheim); biphetamine (Pennwalt); methamphetamine hydrochloride (DESOXYN from Abbott); a mixture of amphetamine adipate and amphetamine sulfate (DELCOBESE—Delco Chemical Company); dextroamphetamine taurate (OBOTAN—Mallinckrodt); d-methamphetamine hydrochloride (FETAMIN—Mission Pharmacal); a mixture of the neutral sulfate salts of dextroamphetamine and amphetamine with the dextro isomer of amphetamine saccarate and d,l-amphetamine aspartate (OBETROL—Obeltrol Pharmaceuticals); racemic mixture of the dextro and levo isomers of amphetamine sulfate (BENZEDRINE—Smith, Kline); benzphetamine hydrochloride (DIDREX—Upjohn); and other comparable compounds listed in the current formularies as bio equivalent thereto.

To further aid in the understanding of the present invention, the following examples are presented to illustrate its operation, it being understood that the use of the term "amphetamine" herein is intended to typify the entire class of compounds which are the bio equivalent of amphetamines including amphetamine when used as anorexants.

Examples I to VIII are attached hereto.

From the foregoing, it becomes apparent that the invention herein described and illustrated fulfills all of my objectives, expressed and implied, in a remarkably unexpected fashion and that I have developed new and useful compositions and therapeutic methods of using the same for providing weight reduction in hosts requiring such therapy.

EXAMPLE I

A white female (age 17) weighing 185 pounds (obviously excessive for her height, age and bone structure) was placed on a daily regimen of 5 mg dextroamphetamine and 300 mg cimetidine. None of the subjective side effects reported for dextroamphetamine (See: Physician's Desk Reference, 33rd Edition, Medical Economics Company, Oradell, N.J. 07649, page 1465) were observed with the exception of mouth dryness.

The subject noted a definite decrease in hunger pangs and resulting food intake. On the 14th day of treatment the subject weighed 180 pounds and on the 45th day of treatment, the subject weighed 176 pounds. (A total loss of 9 pounds).

The regimen was considered successful.

EXAMPLE II

A white female (age 42) weighing 161 pounds (obviously excessive for her height, age and bone structure) was placed on a daily regimen of 5 mg dextroamphetamine and 300 mg cimetidine. None of the subjective side effects reported for dextroamphetamine (See: Physician's Desk Reference, 33rd Edition, Medical Economics Company, Oradell, N.J. 07649, page 1465) were observed with the exception of mouth dryness.

The subject noted a definite decrease in hunger pangs and resulting food intake. On the 43rd day of treatment the subject weighed 154 pounds, on the 71st day of treatment the subject weighed 150 pounds and on the 100th day, the subject weighed 147 pounds (a total loss of 14 pounds).

The regimen was considered successful.

EXAMPLE III

A white female (age 18) weighing 139 pounds (excessive for her height, age and bone structure) was placed on a daily regimen of 5 mg dextroamphetamine and 300 mg cimetidine. None of the subjective side effects reported for dextroamphetamine (See: Physician's Desk Reference, 33rd Edition, Medical Economics Company, Oradell, N.J. 07649, page 1465) were observed with the exception of mouth dryness.

The subject noted a definite decrease in hunger pangs and resulting food intake. On the 43rd day of treatment the subject weighed 136 pounds and on the 93rd day of treatment weighed 129½ pounds ( a loss of almost 10 pounds).

The regimen was considered successful.

EXAMPLE IV

A white female (age 33) weighing 166 pounds (obviously excessive for her height, age and bone structure) was placed on a daily regimen of 15 mg phenteramine resin and 300 mg cimetidine. None of the subjective side effects reported for phenteramine resin (See: Physician's Desk Reference, 33rd Edition, Medical Economics Company, Oradell, N.J. 07649, page 1214) were observed with the exception of mouth dryness.

The subject noted a definite decrease in hunger pangs and resulting food intake. On the 33rd day of treatment the subject weighed 153 pounds (a total loss of 13 pounds).

The regimen was considered successful.

EXAMPLE V

A white female (age 35) weighing 206 pounds (obviously excessive for her height, age and bone structure) was placed on a daily regimen of 15 mg phenteramine resin and 300 mg cinetidine. None of the subjective side effects reported for phenteramine resin (See: Physician's Desk Reference, 33rd Edition, Medical Econom-

METHODS OF OBTAINING ANOREXIC EFFECTS USING A COMBINATION OF AMPHETAMINES AND CIMETIDINE

DESCRIPTION OF THE INVENTION

The present invention relates generally to methods and compositions for supressing the appetite impulse in a mammalian host by the oral administration to such host a novel pharmaceutical preparation containing as its principal active ingredients a small and controlled amount of an anorexant (as hereinafter defined) and cimetidine, whereupon subjective and objective weight loss is obtained without incurring many of the recognized adverse side effects generally associated with the use of any of the known anorexigenic agents.

More particularly, this invention is predicated upon my discovery that significant weight reduction can be obtained in obese mammallian hosts, as in other such hosts requiring or desiring weight reduction for whatever reason, by using substantially less amounts of an anorexant (e.g. amphetamine) than is currently used, in combination with cimetidine whereupon the benefits of anorexant therapy is obtained while substantially all of the recognized adverse side effects of such drugs are eliminated.

Thus, I have found that the oral administration once each day of a dosage containing about 300 mgs of cimetidine (N"-cyano-N-methyl-N'-[2[[(S-methyl-1H-imidazol-4-yl)methyl]thio]-ethyl]guanidine) with a subnormal amount of an anorexant, preferably in conjunction with breakfast, will substantially reduce the feeling of hunger and hence the intake of food to the mammalian host to whom it is administered.

The term "anorexant" as used herein means that class of pharmaceutical compounds which act as an appetite suppressant either by a CNS or an ANS pathway. Representative of the anorexant compounds are amphetamines, and non-amphetamine compositions such as those listed at page 202 of the Physicians Desk Reference, 32d edition, Medical Economics Company, Oradell, N.J. 07649.

The term "amphetamine", is used herein, means dextro- and d, l- amphetamine, racemic admixtures thereof, methamphetamine, non-toxic salts thereof such as the hydrochlorides, adipates, sulfates, tannates, saccharates, aspartates and the like, and the known analog and homolog derivatives thereof which exhibit amphetamine-like effects.

The non-amphetamine anorexants include phentermine hydrochloride, phentermine resin, phenylpropanolamine, phenmetrazine, phendimetrazine tartrate, phenmetrazine hydrochloride, chlorphentermine hydrochloride, mazindol, diethylpropionhydrochloride, and the biochemical equivalents thereof.

In anorexant therapy, whether achieved by the use of the amphetamine or the non-amphetamine class of anorexants, one achieves the desired result in a generally accepted manner at a well recognized dosage level.

However, of concern to the medical profession has been the propensity of these compounds, when administered as the dosage level necessary to achieve the desired result, to produce uncomfortable and unwanted side effects which are hereinafter described in detail.

The amphetamine will hereafter be discussed as generally representative of anorexants as they relate to the present invention.

Amphetamine, a sympathomimetic amine with CNS stimulant activity, has heretofore been used in the treatment of obesity and, as described, are known as "anorexants".

While it has not been fully established, it is believed that the action of anorexants, such as the amphetamines in treating obesity, is primarily one of appetite suppression. Other schools of thought attribute its effect to other central nervous system actions or metabolic effects.

Nonetheless, adult obese subjects instructed in dietary management and treated with anorectic drugs have been found to lose more weight, on the average, than those treated with placebo and diet.

Current regulations, however, do not permit unequivocal conclusions to be made as to the relative importance of the drug and non-drug factors on weight loss.

Used as anoretics, amphetamines per se are subject to a black box warning because of the high potential for abuse and the government has postured that amphetamines should be used in weight reduction programs only in patients for whom alternative therapy has been found ineffective.

Currently, the government further requires a warning that the "administration of d- and d, l- amphetamine for prolonged periods of time in obesity may lead to drug dependence and must be avoided".

In addition to these concerns, the use of amphetamines as anorexants in its normally prescribed dosages gives rise to a myriad of unpleasant side effects. Thus anorexants have been known to cause cardiovascular reactions such as palpitation, tachycardia, and elevated blood pressure; central nervous system reactions such as overstimulation, restlessness, dizziness, insomnia, euphoria, dysphoria, tremor and headache; gastrointestinal reactions such as dryness of the mouth, bad after taste, diarrhea, constipation; allergic reactions such as urticaria; and endocrine reactions such as impotence and altered libido.

These adverse side effects have been detected and reported in all of the various forms of amphetamines which are currently approved for marketing although the degree absorbed varies between the various salts employed.

Accordingly, it is a prime object of the present invention to provide methods and compositions for treating obesity in mammalian hosts which effectively suppress appetite without incurring the untoward side effects heretofore associated with anorexant therapy.

Another object of the present invention is to provide a new and useful anoretic regimen which substantially reduces the daily intake of anorexants by the host seeking anorexia.

Still another object of the present invention is to provide a new and useful anoretic composition which provides the benefits heretofore obtainable from anorexic (e.g. amphetamine) therapy while eliminating substantially all of the adverse side effects heretofore associated therewith.

A further object of the present invention is to provide a synergistic composition for treating obesity comprising cimetidine and a small but effective amount of anorexants.

A still further object of the present invention is to provide a regimen for weight reduction in mammalian hosts in which the amount of anorexant heretofore considered as required dosage is substantially reduced ics Company, Oradell, N.J. 07649, page 1214) were observed with the exception of mouth dryness.

The subject noted a definite decrease in hunger pangs and resulting food intake. On the 7th day of treatment the subject weighed 199 pounds and on the 40th day of treatment weighed 189 pounds (a total loss of 17 pounds).

The regimen was considered successful.

EXAMPLE VI

A white female (age 43) weighing 212 pounds (obviously excessive for her height, age and bone structure) was placed on a daily regimen of 5 mg dextroamphetamine and 300 mg cimetidine. None of the subjective side effects reported for dextroamphetamine (See: Physician's Desk Reference, 33rd Edition, Medical Economics Company, Oradell, N.J. 07649, page 1465) were observed with the exception of mouth dryness.

The subject noted a definite decrease in hunger pangs and resulting food intake. On the 16th day of treatment the subject weighed 200 pounds. On the 46th day of treatment, the subject was removed from the medication. On the 78th day of the program, the subject weighed 194 pounds (a total weight loss of 20 pounds).

The regimen was considered successful.

EXAMPLE VII

A white female (age 17) weighing 176 pounds (obviously excessive for her height, age and bone structure) was placed on a daily regimen of 50 mg phenmetrazine and 300 mg cimetidine. None of the subjective side effects reported for phenmetrazine (See: Physician's Desk Reference, 33rd Edition, Medical Economics Company, Oradell, N.J. 07649, Page 635) were observed with the exception of mouth dryness.

The subject noted a definite decrease in hunger pangs and resulting food intake. On the 38th day of treatment the subject weighed 170 pounds and on the 72nd day of treatment weighed 167 pounds.

The regimen was considered successful.

What is claimed:

1. A method of suppressing the appetite of a mammalian host as an adjunct to a weight control program comprising administering orally to said host once daily (a) up to 5 mg of an anorexant which is substantially less than the normal daily dosage of said anorexant concurrently with (b) from 150 mg to 300 mg of cimetidine, said anorexant being selected from the group consisting of amphetamines, biphetamines and the non-toxic biologically acceptable salts thereof.

2. A method according to claim 1 in which said anorexant consists of up to 5 mg of dextroamphetamine.

3. A method according to claim 1 in which said anorexant consists of up to 5 mg of d,l-amphetamine.

4. A method according to claim 1 in which said anorexant and said cimetidine are administered in a common dosage form.

5. A method according to claim 4 in which said dosage form comprises a gelatin capsule.

* * * * *